United States Patent [19]
Nair et al.

[11] Patent Number: 5,550,128
[45] Date of Patent: Aug. 27, 1996

[54] ENANTIOMERS OF GAMMA METHYLENE 10-DEAZA AMINOPTERIN AND PROCESS FOR PREPARING THE SAME

[76] Inventors: Madhavan G. Nair; Indira G. Nair, both of 7005 Charleston Oaks Dr. N.; Ratna Pati, 2101 Woodford Ct., all of Mobile, Ala. 36695

[21] Appl. No.: 303,403

[22] Filed: Sep. 9, 1994

[51] Int. Cl.$^6$ .................................................. C07D 475/08
[52] U.S. Cl. ............................................ 514/249; 544/260
[58] Field of Search ............................. 544/260; 514/249

[56] References Cited

U.S. PATENT DOCUMENTS

| | | | |
|---|---|---|---|
| 4,369,319 | 1/1983 | DeGraw | 544/260 |
| 4,746,659 | 5/1988 | DeGraw | 514/249 |
| 4,959,472 | 9/1990 | Wood et al. | 544/258 |
| 4,996,207 | 2/1991 | Nair | 544/258 |
| 5,073,554 | 12/1991 | Nair | 514/249 |

FOREIGN PATENT DOCUMENTS 2081385   2/1985   Japan ..................................... 544/260

OTHER PUBLICATIONS

Winter et al., Jour–Biolog. Chem. vol. 261 p. 11189 (1986).
Stinson et al Chem. & Eng. News Sep. 27, 1993 pp. 38–64.

*Primary Examiner*—Donald G. Daus

[57] ABSTRACT

The biologically active enantiomer of γ-methylene-10-deazaaminopterin (L-MDAM) possessing the L configuration at the γ-methyleneglutamate moiety, which is identical to the absolute configuration at the α-position of the γ-methyleneglutamic acid isolated from peanut seedlings is provided as well as procedures for its preparation. The compound does not undergo polyglutamylation, is twice as effective as an inhibitor of recombinant human dihydrofolate reductase, and exhibits outstanding growth inhibitory activity in a large variety of human tumor cells in culture. The biochemical and pharmacological results established the utility of L-MDAM as a therapeutic agent for the treatment of human neoplastic diseases.

7 Claims, No Drawings

ENANTIOMERS OF GAMMA METHYLENE 10-DEAZA AMINOPTERIN AND PROCESS FOR PREPARING THE SAME

This invention is related to antineoplastic agents in the antifolate class of drugs and process for their preparation.

ORIGIN OF INVENTION

This invention pertains of enantiomers of γ-methylene-10-deazaaminopterin and the use of these compounds as anti-cancer agents.

In 1974 DeGraw, Kisliuk, Gaumont, Baugh and Nair reported the chemical synthesis and preliminary biological evaluation of 10-deazaaminopterin in *Journal of Medicinal Chemistry*, volume 17, page 552. Further improvement of the antitumor activity of 10-deazaaminopterin by introducing alkyl substituents at the 10-position was reported by DeGraw and coworkers in 1982 (*J. Med. Chem.* 25, 1227, 1982). These improved 10-alkyl-10-deazaaminopterins were patented by DeGraw and Sirotnak in 1983 and 1984. [U.S. Pat. No. 4,369,319 (1983) and U.S. Pat. No. 4,433, 147 (1984)]. The above 10-deazaaminopterins contain a L-glutamate moiety as an integral part of their structural frame work and on administration of these compounds to warm blooded animals, and to a number of tumor cells in culture, they were elaborated to their respective poly-γ-glutamate derivatives. In 1973, Baugh, Krumdieck and Nair discovered that the well-known anticancer drug methotrexate, which is a non-trivial analogue of 10-deazaaminopterin, was metabolized to its poly-γ-glytamyl derivatives by adding additional glutamate residues to the existing L-glutamate moiety of methotrexate. (Baugh, Krumdieck, and Nair, *Biochem. Biophys, Res. Commun.* 52, 27, 1973).

A detailed study of the biochemical pharmacology of methotrexate polyglutamates established that these metabolite are formed as a function of concentration and time and they do not readily efflux out of mammalian cells [J. Jolivet, et al. *Clinical Invest.* 70, 351, (1982)].

Methotrexate polyglutamates, in addition to inhibiting the target enzyme dihydrofolate reductase (DHFR), also inhibits folate dependent enzymes such as thymidylate synthase (TS) and ALCAR-formyltransferase, thus potentiating the toxicity of the drug. All classical folate antagonists that possess a L-glutamate moiety when administered to a warm blooded animal undergo polyglutamylation and this process is a major determinant of antifolate toxicity. Since the formation of poly-γ-glutamates of classical folate antagonists results in the loss of pharmacological control due to diminished drug clearance and inhibition of other folate dependent enzymes by these metabolites recently a number of classical antifolate inhibitors of DHFR that are incapable of polyglutamylation were designed, synthesized and evaluated for anticancer activity. [M. G. Nair and Ann Abraham, U.S. Pat. No. 4,996,207 (1991); M. G. Nair, U.S. Pat. No. 5,073,554 (1991)]. These non-polyglutamylatable compounds in general, and the γ-methylene-10-deazaaminopterins in particular, exhibited enhanced efflux characteristics, and lower host toxicity without compromising therapeutic effectiveness. In fact both γ-methylene-10-deazaaminopterin (MDAM) and γ-methylene-10-ethyl-10-deazaaminopterin (MEDAM) were tolerated by animals at higher doses and they exhibited superior in vivo antitumor activity relative to the polyglutamylatable MTX in animals bearing L1210 and P388 leukemia. [Ann Abraham, M. G. Nair, et al. *Advanced in Exp. Med. and Biol.* 663–666 (1993)]. When MDAM was given as single iv push daily for 5 days at the maximum tolerated dose, to nude mice bearing human HCT-8 Ileocecal xenograft, an excellent antitumor response of 75% was obtained. Of these 25% of animals exhibited complete tumor regression (Table-1).

TABLE 1

Antitumor Activity of MDAM by I.V. Push, Daily × 5 against Human HCT-8 Ileocecal Xenograft

| Drug (mg/kg) | MIR (%) | TD (Day) | CR (%) | PR (%) | MWL (%) |
|---|---|---|---|---|---|
| Control | — | 3.2 ± 0.5 | — | — | 3.8 ± 1.8 |
| MTX$_1$ | 29.8 ± 8.6 | 4.6 ± 0.6 | 0 | 0 | 14.0 ± 3.0 |
| MDAM$_{30}$ | 58.8 ± 9.2 | 6.2 ± 0.9 | 0 | 0 | 8.6 ± 2.8 |
| MDAM$_{40}$ | 79.2 ± 7.5 | 7.1 ± 0.5 | 25 | 25 | 8.8 ± 2.2 |
| MDAM$_{50}$ | 79.2 ± 6.2 | 8.4 ± 0.4 | 25 | 50 | 8.9 ± 1.8 |

MIR: Maximum inhibitory rate. TD: Tumor doubling time.
CR: Complete Regression. PR Partial Regression.
MWL: Maximum Weight Loss.

More striking results were obtained when MDAM was administered at dose of 2 mg/kg/day by continuous 5 day iv infusion which resulted in 38% complete tumor regression and 38% partial tumor regression in nude mice bearing human HCT-8 Ileocecal xenograft. In both experiments described above, methotrexate did not exhibit any measurable antitumor activity, clearly establishing the potential clinical superiority of MDAM versus MTX for the indication of human colorectal carcinoma.

TABLE 2

Antitumor Activity of MDAM by C.I. × 5d against HUMAN HCT-8 Ileocecal Xenograft

| Drug (mg/kg) | MIR (%) | TD (Days) | CR (%) | PR (%) | MWL (%) |
|---|---|---|---|---|---|
| Control | — | 3.2 ± 0.5 | — | — | 3.8 ± 1.8 |
| MTX$_{0.1}$ | 50.6 ± 9.6 | 4.8 ± 0.4 | 0 | 0 | 11.2 ± 2.4 |
| MTX$_{0.2}$ | 52.8 ± 8.5 | 5 ± 0.5 | 0 | 0 | 14.2 ± 1.8 |
| MTX$_{0.25}$* | — | — | 0 | 0 | 9.2 ± 2.8 |
| MDAM$_{0.5}$ | 49.8 ± 8.2 | 5.3 ± 0.9 | 0 | 0 | 6.6 ± 2.6 |
| MDAM$_1$ | 56.4 ± 7.8 | 6.0 ± 0.7 | 0 | 0 | 11.6 ± 2.2 |
| MDAM$_2$ | 81.7 ± 7.2 | 12.4 ± 5.8 | 38 | 38 | 20.8 ± 1.8 |

MIR: Maximum inhibitory rate.
TD: Tumor doubling time.
CR: Complete Regression.
PR: Partial Regression.
MWL: Maximum Weight Loss.
*100% death.

The mechanism of action of MDAM is inhibition of the enzyme dihydrofolate reductase, (DHFR). D,L-MDAM showed inhibitory activity towards recombinant human DHFR similar to that of methotrexate. L-MDAM exhibited DHFR inhibitory activity similar to D,L-MDAM and MTX; and as expected it was exactly twice as active as D,L-MDAM (Table 3).

TABLE 3

Inhibition of Recombinant Human Dihydrofolate Reductase by L-MDAM, D,L-MDAM, and MTX

| Compound | IC$_{50}$ (M)* | IC$_{50}$ Compound/ IC$_{50}$ MTX |
|---|---|---|
| L-MDAM | $2.2 \times 10^{-8}$ | 1.29 |
| D,L-MDAM | $4.4 \times 10^{-8}$ | 2.58 |
| MTX | $1.7 \times 10^{-8}$ | 1.00 |

Enzyme assay was performed spectrophotometrically in a solution containing 50 μM dihydrofolate, 80 μM NADPH, 0.05 M Tris HCl. 0.01 M 2-mercaptoethanol and 0.001 M EDTA at pH 7.4 at 30°. The reaction was initiated with an amount of enzyme yielding a change in OD at 340 nm of 0.015/min. Pure human recombinant enzyme was used.

When D,L-MDAM was evaluated using Human Tumor Disease Oriented in vitro screen, it exhibited more potent activity relative to methotrexate in several tumor cell lines. The relative efficacy D,L-MDAM in inhibiting a number of human tumor cell lines in culture is summarized in Table-4. These $Gl_{50}$ values show that MDAM has equivalent or greater potency than methotrexate in inhibiting the growth of a number of tumor cells in culture. If the in vivo antitumor activity of MDAM in mice bearing various tumors, the results of in vitro Antitumor Screen, and target enzyme (dihydrofolate reductase) inhibition are taken together, it is clear that MDAM is superior to methotrexate, and should have clinical utility as an anticancer agent, Since D,L-MDAM is a 1:1 mixture of D-MDAM and L-MDAM and only L-MDAM is expected to be active, an unambiguous synthesis of L-MDAM was carried out, and the in vitro tumor cell growth inhibitory data presented in Table - 5 clearly establishes that indeed L-MDAM is the biologically active enantiomer of D,L-MDAM (vide infra). Further, by analogy to methotrexate (rheumatrex) L-MDAM should be useful in the treatment of autoimmune diseases such as rheumatoid arthritis and inflammatory diseases such as asthma.

Independent, further evidences to the identity of L-MDAM as the biologically active enantiomer of the racemic mixture of D,L-MDAM (previously described as MDAM; Ref, U.S. Pat. No. 4,996,207) was obtained by the following data. L-MDAM inhibited the transport of radio-labeled folinic acid to H35 hepatoma cells exhibiting an $l_{50}$ value of 2.3 microMolar, compared to the $l_{50}$ value of 5.5 microMolar for D,L-MDAM. This reduction in $l_{50}$ value of approximately one-half is entirely consistent with L-MDAM being the isomer that is transported to the cell to exhibit antitumor activity. The cytotoxicity of L-MDAM versus D,L-MDAM was also compared. Dramatic and unexpected potentiation of activity was observed with L-MDAM. The $l_{50}$ value for growth inhibition ($Gl_{50}$) was 39 nM for D,L-MDAM. Under identical conditions L-MDAM exhibited an $l_{50}$ value of 8.0 nM in inhibiting the growth of H35 hepatoma cells in culture. Taken together, these unexpected and novel results establish that the biologically active compound present in the racemic mixture of MDAM is the L-enantiomer described in claim number 1.

Accordingly, this invention provides a process for treating leukemia, solid and ascitic tumors, rheumatoid arthritis, and asthma which compromises administering to a warm blooded animal with evidences of neoplastic, auto-immune or inflammatory diseases a therapeutic non-toxic amount of L-MDAM as such or in the form of a pharmacologically acceptable salt thereof. The salts may be formed with one or more amino groups of the pteridine ring, with hydrochloric, hydrobromic, nitric, phosphoric, sulfonic, salicylic, citric, maleic, phthalic, benzoic or toluene sulfonic acids.

L-MDAM as such, or as its salts with the above acids may be administered to a warm-blooded animal by parental (intraperitoneal, intravenous, intrathecal, subcutaneous, intramuscular) or oral routes. Soluble formulations of L-MDAM such as its monosodium or disodium salts in 5% sucrose or 0.9% saline or distilled water may be administered by repeated injections or continuous infusion to obtain the desired non-toxic therapeutic efficacy in ameliorating neoplastic or auto-immune or inflammatory diseases. A dosage in the amount of 0.1 mg/kg/day to about 10 gr/kg/day is considered the therapeutic range of L-MDAM for the treatment of neoplastic, auto-immune or inflammatory diseases.

L-MDAM can be administered in composite forms or in dosage unit forms. A sterile non-toxic carrier may be added to L-MDAM, it salts with organic and inorganic acids, or its monometallic or dimetallic salts with sodium, potassium, magnesium, calcium, etc. The added carrier may be a solid, semi-solid or liquid that may serve as a vehicle, excipient or medium. Gelatin, methylcellulose, mineral oil, sorbitol, mannitol, gum aracia, lactose, dextrose, talc, magnesium stearate, oil of theobroma, propyl hydroxybenzoate and methyl cellulose may serve as carriers. L-MDAM and its salts thereof and a carrier or diluent can be encapsulated, enclosed in a paper or other container, capsule, cachet, gelatin, or sachet when intended for use in dosage units and they can take the form of tablets, capsules, suppositories, or cachets.

The process of the invention of L-MDAM (4-amino-4-deoxy-10-deazapteroyl-γ-methylene-L-glutamic acid) comprises of converting naturally occurring γ-methylene-L-glutamic acid isolated from peanut seedlings to the corresponding diethyl ester hydrochloride followed by its coupling to 4-amino-4-deoxy-10-deazapteroic acid prepared according to the procedure of Nair, described in *Journal of Organic Chemistry* 50, 1879 (1985) by the isobutylchloroformate method, and subsequent hydrolysis of the coupled product and purification by reverse phase column chromatography. The reaction sequence for the synthesis of L-MDAM is shown in Scheme-1.

TABLE 4

Human Disease Oriented in vitro Antitumor Screen
Data is Standardized relative to MTX

| Cell Line | MDAM |
| --- | --- |
| Leukemia | |
| CCRF-CEM | 36 |
| HL-60 (TB) | 300 |
| K-562 | >300 |
| MOLT-4 | 14 |
| SR | 107 |
| Non-Small Cell Lung Cancer | |
| A549/ATCC | 27 |
| NCI-H322M | 23 |
| Small Cell Lung Cancer | |
| DMS 114 | 3 |
| DMS 273 | 8 |
| Ovarian Cancer | 5 |
| OVCAR-8 | |
| Colon Cancer | |
| DLD-1 | 28 |
| HCC-2993 | 51 |
| HCT-116 | 72 |
| HT-29 | 38 |
| SW-620 | 27 |
| SF-268 | 9 |
| SF-295 | 5 |
| SF-539 | 2 |
| SNB-19 | 3 |
| Melanoma | 50 |
| LOX IM VI | |
| Renal Cancer | |
| 786-O | 42 |
| ACHN | 7 |

A 48 h continuous drug exposure protocol was used combined with an SR13 protein assay to estimate cell growth or viability.

L-MDAM inhibited the growth of the following human tumor cells in culture exhibiting $Gl_{50}$ values much lower than 10 nM ($10 \times 10^{-9}$M). It is also active against the adriamycin resistant MCF-7 human breast cancer cells ($Gl_{50} = 74 \times 10^{-9}$).

TABLE 5

Human Disease Oriented in vitro Antitumor Screen
L-MDAM

| Leukemia | Ovarian Cancer |
| --- | --- |
| CCRF-CEM | IGROVI |
| HL-60 TB | OVCAR-5 |
| MOLT-4 | OVCAR-8 |
| RPMI-8226 | Renal Cancer |
| SR | 786-O |
| Non-Small Cell Lung Cancer | ACHN |
| HOP-62 | SN-12C |
| NCI-H460 | TK-10 |
| Colon Cancer | Prostate Cancer |
| HCT-116 | DU 145 |
| HCT-15 | Breast Cancer |
| HT-29 | MCF-7 |
| SW-620 | MCF-7/ADR-RBS |
| Melanoma | MDA-MB-231/ATCC |
| LOX MI VI | MDA-N |
| M14 | CNS Cancer |
| ZIACC-62 | SF-268 |
| | SF-295 |
| | SF-539 |
| | U-251 |

The 10-deazaaminopterins (MDAM and MEDAM) used in previous studies were mixtures of enantiomers in the case of MDAM and diastereomers in the case of MEDAM due to the asymmetry of the α-carbon of γ-methylene glutamate of MDAM and asymmetries at α-carbon of γ-methylene glutamate and at C10 for MEDAM. Although it is well established that only those antifolates bearing the L glutamate moiety are biologically active, it was unclear which enantiomer of MDAM or which diasteromer of MEDAM actually contributed to the antitumor activity. Therefore an unambiguous synthesis of MDAM bearing the "L"-γ-methyleneglutamic acid [isolated from peanut seedlings according to a literature procedure [H. C. Winter and E. E. Dekker. *J. Biol. Chem.* 261., 11189, (1986)] was carried out (scheme-1). γ-Methylene-L-glutamic acid was converted to its corresponding diethyl ester hydrochloride by reacting with ethyl alcohol and thionyl chloride for 18 hrs or by treating with ethanol saturated with gaseous HCl for 18 hrs at room temperature. Any alkyl or aryl diester of γ-methylene-L-glutamic acid can be prepared by this procedure by substituting ethyl alcohol with an aliphatic or aromatic alcohol in the above procedure. Examples of aliphatic alcohols are methanol, propanol, isopropanol, butanol, isobutanol, tetriarybutanol, cyclopropanol, cyclopentanol, cyclohexanol, and long chain aliphatic alcohols such as octanol, decanol, dodecanol, etc. Aromatic alcohols may be phenol, benzyl alcohol, or a substituted benzyl alcohol such as p-nitrobenzyl alcohol. Any of the aliphatic or aromatic diesters of γ-methylene-L-glutamic acid may be used for the preparation of the 'L' enantiomer of γ-methylene-10-deazaaminopterin (MDAM) or a diastereomer of MEDAM. 4-Amino-4-deoxy-10-deazapteroic acid was prepared according to the procedure of Nair (*J. Org. Chem.* 50, 1879, 1984). In a typical procedure 310 mg (1 mmol.) of 4-amino-4-deoxy-10-deazapteroic acid was dissolved in 100 mL of dimethylforamide at 80° C., and 1.25 equivalents of triethylamine was added. After cooling to about 0° C. in an icebath 1 equivalent of isobutylchloroformate was added and the solution was allowed to warm to 25° C. To this solution was added 1.5 equivalents of triethylamine. The reaction mixture was allowed to stir at room temperature for 18 hrs and then evaporated to dryness. On addition of 25 gr. of ice, a yellow solid was formed which was filtered, washed and dried.

In the above coupling reaction, isobutylchloroformate can be substituted with an alkyl or aryl chloroformates such as ethyl chloroformate or benzylchloroformate. The coupling reaction can also be carried out in solvents such as pyridine, with the use of a carbodiimide as the reagent. An example of a carbodiimide is dicyclohexyl carbodiimide. Other coupling reagents such as carbonyldiimidazole, and diphenylphosphorazidate (DPPA) can also be used to couple 4-amino-4-deoxy-10-deaza pteroid acid with an appropriate diester of γ-methylene-L-glutamic acid.

The crude coupled product containing the unreacted 4-amino-4-deoxy-10-deazapteroic acid and the desired diethyl-γ-methylene-10-deazaaminopterin was hydrolyzed with a mixture of 100 mL of 0.1N NaOH and 30 mL of acetonitrile for 18 hrs at 25° C. Removal of acetronirile under reduced pressure at 40° C. followed by acidification of the clear hydrolysate with glacial acetic acid gave a yellow precipitate, which was purified by chromatography on a C18 silica gel column. Substitution of 4-amino-4-deoxy-10-deazapteroic acid with 4-amino-4-deoxy-10-ethyl-10-deazapteroic acid in the above reaction and subsequent workup of the product as described for L-MDAM should yield the diastereomers of γ-methylene-10-ethyl-10-deazaaminopterin possessing the L-γ-methylene glutamate moiety. These compounds are 4-amino-4-deoxy-10-(R)-ethyl-10-deazapteroyl -γ-methylene-L-glutamiacid (R,L-MEDAM) and 4-amino-4-deoxy-10-(S)-ethyl-10-deazapteroyl-γ-methylene-L-glutamic acid (S,L-MEDAM).

Substitution of 4-amino-4-deoxy-10-deazapteroic acid with 4-amino-4-deoxy-$N^{10}$-methylpteroic acid in the above reaction and subsequent workup should yield the non polyglutamylatable methotrexate analogue; 4-amino-4-deoxy-$N^{10}$-methylpteroyl-γ-methylene-L-glutamic acid (L-MMTX). A large number of other pteroic acids can also be coupled to a diester of γ-methylene-L-glutamic acid to obtain a series of nonpolyglutamylatable classical antifolates possessing the γ-methylene-glutamate moiety. These pteroic acids may include, but not limited to a) 4-amino-4-deoxy-5,10-dideazapteroic acid; b) 4-amino-4-deoxy-8-deazapteroic acid; c) 4-amino-4-deoxy-8,10-dideazapteroic acid; d)4-amino-4-deoxypteroic acid; and e) 4-[2-(2,4-diamino-6,7-dihydro-5H-cyclopenta [d] pyrimidin-5-yl-ethyl] benzoic acid.

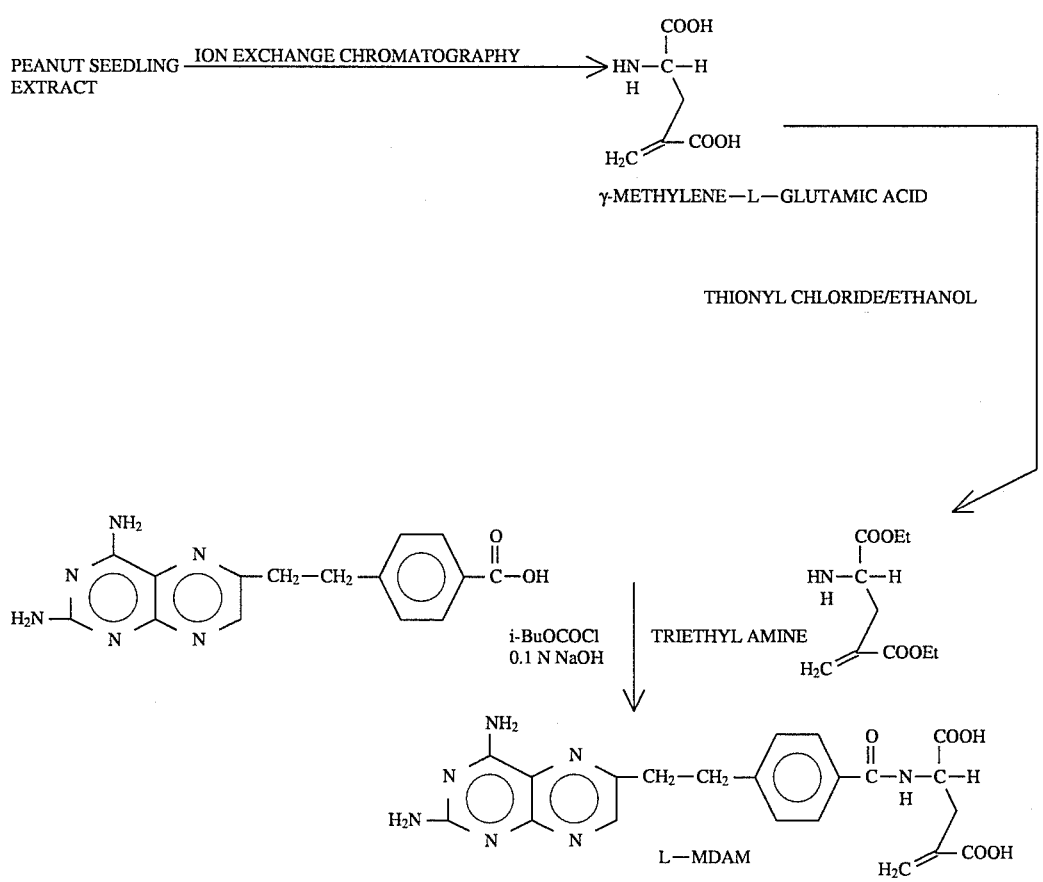

Scheme 1

EXAMPLE 1

Diethyl-γ-methylene-L-glutamate hydrochloride

In a 100 mL round bottomed flask containing a magnetic stirring bar, 320 mg (2 mmol) of γ-methylene-L-glutamic acid isolated from peanut seedling according to the procedure of Winter and Dekker, (*J. Biol. Chem.* 261, 11189, 1986) was suspended followed by the addition of 50 mL of anhydrous ethyl alcohol. The resulting suspension was stirred at 0° C. using an ice-bath until the inside temperature of the reaction mixture measured ~4° C. To this mixture was added 10 mL of thionylchloride, dropwise, while maintaining the temperature below 10° C., and the solution was stirred for 18 hrs at 25° C. Benzene (10 mL) was added, and the clear solution was evaporated to dryness under reduced pressure. The resultant crystalline solid was judged to be a single compound on examination by TLC and it co-chromatographed with an authentic sample of D,L-diethyl-γ-methylene-glutamate, the synthesis of which was previously reported by Nair and Abraham [*J. Med. Chem.* 34, 222 (1991)]. The mass spectrum of this product exhibited a protonated molecular ion at m/z 217.00. After thorough drying in vacuum over $P_2O_5$, it was used directly for the coupling reaction.

L-γ-Methylene- 10-deazaaminopterin (L-MDAM)

To a solution of 310 mg (1 mmol) of 4-amino-4-deoxy-10-deazapteroic acid in 100 mL of dry dimethyl formamide (DMF) was added 1.25 equivalent of triethylamine and cooled to 0° C. with the aid of an ice-bath. Under stirring, one equivalent of freshly distilled isobutylchloroformate was added and the reaction mixture was allowed to warm up to 25° C. during a period of ~45 minutes. To this mixed-anhydride solution was added 2 equivalent (2 mmol) of triethylamine followed by 1.5 equivalents of diethyl-L-γ-methyleneglutamate hydrochloride dissolved in 10 mL of DMF. The reaction mixture was allowed to stir at 25° C. for 18 hrs and 0.5 mmol of triethylamine was added. After ten minutes the remaining 0.5 mmol of diethyl-L-γ-methyleneglutamate was added to the reaction mixture, stirred for 18 hrs and evaporated to dryness under reduced pressure at 70° C. The residue was triturated with 25 mL of 5 % $NaHCO_3$, filtered, and washed with 10 mL of distilled water. The wet residue thus obtained was transferred to an Erlenmeyer flask, and stirred with a mixture of 1 00 mL of 0.1N NaOH and 35 mL of acetonitrile for 18 hr. After removal of acetonitrile under reduced pressure at 35° C., the resultant solution was acidified with glacial acetic acid to pH 4.0 and chilled. The precipitate thus obtained was filtered, washed with water, dissolved in 3 mL of 5% $NaHCO_3$ and applied on a C18 silicagel column that was equilibrated with 10% acetonitrile in distilled water. The column was eluted with the same solvent mixture, and fractions corresponding to the product (as judged by HPLC) was pooled, concentrated and acidified to pH 4.0 with glacial HOAc. The precipitated L-γ-methylene-10-deazaaminopterin (L-MDAM) was filtered, washed with distilled water and dried. Yield 280 mg;mp>300° C.

The purity of L-γ-methylene-10-deazaaminopterin (L-MDAM) was determined by HPLC and the pure material was characterized by NMR, mass spectrometry, UV spectroscopy and elemental analysis.

4-Amino-4-deoxy-10-deazapteroyl-γ-methylene-L-glutamic acid (L-MDAM) exhibited the following UV absorption peaks in 0.1 NaOH.

| λmax 370 nm | (ε = 6,850) |
| λmax 254 nm | (ε = 30,650) |

The mass spectrum of 4-amino-4-deoxy-10-deazapteroyl-γ-methylene-L-glutamic acid (L-MDAM) showed the protonated molecular ion at m/z=452 (MH$^+$), that is in agreement with the structure and the molecular formula $C_{21}H_{21}N_7O_5$, the mass of which is 451.

4-Amino-4-deoxy-10-deazapteroyl-γ-methylene-L-glutamic acid (L-MDAM) analyzed as follows:

|  | calcd. | found |
|---|---|---|
| $C_{21}H_{21}N_7O_5$ | % C 55.87 | 55.68 |
|  | % H 4.66 | 4.59 |
|  | % N 21.73 | 21.95 |

Having regard to the foregoing disclosure, the following is claimed as inventive and patentable embodiments thereof:

We claim:

1. 4-Amino-4-deoxy-10-deazapteroyl-γ-methylene-L-glutamic acid (L-MDAM) having the following chemical structure, wherein the γ-methyleneglutamate moiety has the "L" configuration.

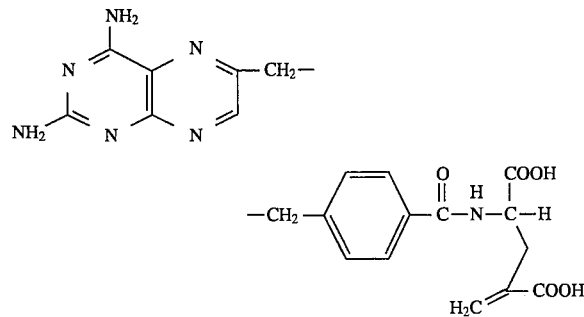

2. 2-Amino-4-deoxy-10-ethyl-10-deazapteroyl-γ-methylene-L-glutamic acid (L-MEDAM) having the following chemical structure wherein the γ-methyleneglutamate moiety has the "L" configuration.

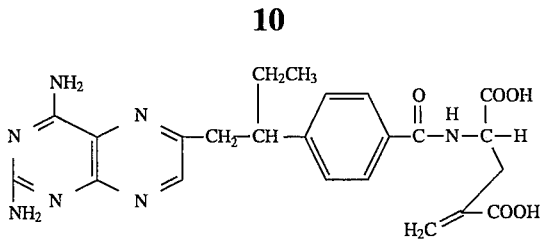

3. A compound having the following chemical structure wherein the γ-methyleneglutamate moiety has the "L" configuration and 'R' is selected from a group consisting of methyl, propyl and butyl.

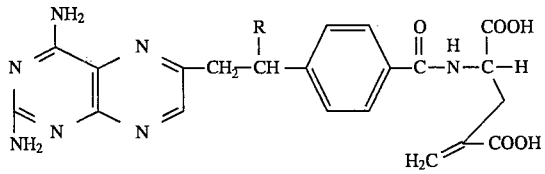

4. A pharmaceutical composition for treating neoplastic growth that responds to antifolates, a therapeutically effective and non toxic amount of 4-amino-4-deoxy-10-deazapteroyl-γ-methylene-L-glutamic acid (L-MDAM) with or without a pharmaceutically acceptable carrier or diluent to inhibit the said neoplastic growth.

5. A pharmaceutical composition for treating neoplastic growth that responds to antifolates, a therapeutically effective and non toxic amount of 4-amino-4-deoxy-10-ethyl-10-deazapteroyl-γ-methylene-L-glutamic acid (L-MEDAM) with or without a pharmaceutically acceptable carrier or diluent to inhibit the said neoplastic growth.

6. A process for treating neoplastic growth that responds to antifolates which comprises administering orally or parenterally to a warm blooded animal having evidence of neoplastic growth a therapeutically effective and relatively nontoxic amount of 4-amino-4-deoxy-10-deazapteroyl-γ-methylene-L-glutamic acid (L-MDAM) to inhibit the said neoplastic growth.

7. A process for treating neoplastic growth that responds to antifolates which comprises administering orally or parenterally to a warm blooded animal having evidence of neoplastic growth a therapeutically effective and relatively nontoxic amount of 4-amino-4-deoxy-10-ethyl-10-deazapteroyl-γ-methylene-L-glutamic acid (L-MEDAM) to inhibit the said neoplastic growth.

* * * * *